US010548761B2

(12) United States Patent
Kovarik

(10) Patent No.: US 10,548,761 B2
(45) Date of Patent: *Feb. 4, 2020

(54) METHOD AND SYSTEM FOR REDUCING THE LIKELIHOOD OF COLORECTAL CANCER IN A HUMAN BEING

(71) Applicant: Joseph E. Kovarik, Englewood, CO (US)

(72) Inventor: Joseph E. Kovarik, Englewood, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/142,171

(22) Filed: Sep. 26, 2018

(65) Prior Publication Data
US 2019/0029871 A1 Jan. 31, 2019

Related U.S. Application Data

(63) Continuation-in-part of application No. 15/395,419, filed on Dec. 30, 2016, now Pat. No. 10,086,018, which is a continuation-in-part of application No. 14/752,192, filed on Jun. 26, 2015, now Pat. No. 9,549,842, which is a continuation-in-part of application No. 14/225,503, filed on Mar. 26, 2014, now Pat. No. 9,445,936, which is a continuation of application No. 13/367,052, filed on Feb. 6, 2012, now Pat. No. 8,701,671, which is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077, which is a continuation-in-part of application No. 14/574,517, filed on Dec. 18, 2014, now Pat. No. 9,408,880, which is a continuation-in-part of application No. 15/228,454, filed on Aug. 4, 2016, now Pat. No. 9,585,920, which is a continuation-in-part of application No. 14/611,458, filed on Feb. 2, 2015, which is a continuation-in-part of application No. 14/502,097, filed on Sep. 30, 2014, now Pat. No. 9,010,340, which is a continuation of application No. 14/307,651, filed on Jun. 18, 2014, now Pat. No. 8,936,030, which is a continuation-in-part of application No. 14/079,054, filed on Nov. 13, 2013, now Pat. No. 8,757,173, which is a continuation of application No. 13/425,913, filed on Mar. 21, 2012, now Pat. No. 8,584,685.

(60) Provisional application No. 62/274,550, filed on Jan. 4, 2016, provisional application No. 61/439,652, filed on Feb. 4, 2011, provisional application No. 61/556,023, filed on Nov. 4, 2011, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013, provisional application No. 62/275,341, filed on Jan. 6, 2016, provisional application No. 61/467,767, filed on Mar. 25, 2011.

(51) Int. Cl.
A61F 5/56 (2006.01)

(52) U.S. Cl.
CPC .................................. A61F 5/566 (2013.01)

(58) Field of Classification Search
None
See application file for complete search history.

(56) References Cited

U.S. PATENT DOCUMENTS

| | | |
|---|---|---|
| 3,178,341 A | 4/1965 | Hamill et al. |
| 3,832,460 A | 8/1974 | Kosti |
| 4,136,162 A | 1/1979 | Fuchs et al. |
| 4,163,777 A | 8/1979 | Mitra |
| 4,568,639 A | 2/1986 | Lew |
| 4,687,841 A | 8/1987 | Spilburg et al. |
| 4,720,486 A | 1/1988 | Spilburg et al. |
| 4,995,555 A | 2/1991 | Woodruff |
| 5,002,970 A | 3/1991 | Eby, III |
| 5,277,877 A | 1/1994 | Jeffrey et al. |
| 5,614,501 A | 3/1997 | Richards |
| 5,719,196 A | 2/1998 | Uhari |
| 6,054,143 A | 4/2000 | Jones |
| 6,139,861 A | 10/2000 | Friedman |
| 6,210,699 B1 | 4/2001 | Acharya |
| 6,287,610 B1 | 9/2001 | Bowling et al. |
| 6,569,474 B2 | 5/2003 | Clayton et al. |

(Continued)

FOREIGN PATENT DOCUMENTS

| | | |
|---|---|---|
| WO | PCT/US2008/080362 | 4/2009 |
| WO | WO 2011/020780 | 2/2011 |
| WO | WO 2013/107750 | 7/2013 |

*Primary Examiner* — Brian Gangle
(74) *Attorney, Agent, or Firm* — Sheridan Ross P.C.

(57) ABSTRACT

A system and method for reducing the likelihood of colorectal cancer in a human being includes the modification of an individual's gut microbes by employing a Clustered Regularly Interspaced Short Palindromic Repeats-CRISPR-associated system (CRISPR-Cas) or Clustered Regularly Interspaced Short Palindromic Repeats from *Prevotella* and *Francisella* 1 (CRISPR/Cpf1) system to modify only bacterial genes of bacteria that reside in the human gut that are non-homologous to those encompassed in the human genome, and in particular, to administer a therapeutically effective amount of a bacterial formulation comprising *F. prausnitzii* that has been modified to produce one of alliin or butyrate.

7 Claims, 1 Drawing Sheet

(56) References Cited

U.S. PATENT DOCUMENTS

| | | |
|---|---|---|
| 6,599,883 B1 | 7/2003 | Romeo |
| 6,722,577 B2 | 4/2004 | Dobyns, III |
| 6,919,373 B1 | 7/2005 | Lam et al. |
| 7,087,249 B2 | 8/2006 | Burrell |
| 7,267,975 B2 | 9/2007 | Strobel et al. |
| 7,353,194 B1 | 4/2008 | Kerker et al. |
| 7,540,432 B2 | 6/2009 | Majerowski et al. |
| 7,820,420 B2 | 10/2010 | Whitlock |
| 7,862,808 B2 | 1/2011 | Isolauri et al. |
| 7,901,925 B2 | 3/2011 | Bojrab |
| 8,034,606 B2 | 10/2011 | Park et al. |
| 8,197,872 B2 | 6/2012 | Mills et al. |
| 8,349,313 B2 | 1/2013 | Smith et al. |
| 8,420,074 B2 | 4/2013 | Rehberger et al. |
| 8,454,729 B2 | 6/2013 | Mittelmark et al. |
| 8,481,299 B2 | 7/2013 | Gueniche |
| 8,496,914 B2 | 7/2013 | Bonfiglio |
| 8,585,588 B2 | 11/2013 | Kovarik et al. |
| 8,685,389 B2 | 4/2014 | Baur |
| 8,701,671 B2 | 4/2014 | Kovarik |
| 8,716,327 B2 | 5/2014 | Zhao |
| 8,758,764 B2 | 6/2014 | Masignani et al. |
| 8,815,538 B2 | 8/2014 | Lanzalaco et al. |
| 8,865,211 B2 | 10/2014 | Tzannis |
| 8,951,775 B2 | 2/2015 | Castiel |
| 8,999,372 B2 | 4/2015 | Davidson |
| 9,011,834 B1 | 4/2015 | McKenzie et al. |
| 9,017,718 B2 | 4/2015 | Tan |
| 9,028,841 B2 | 5/2015 | Henn et al. |
| 9,131,884 B2 | 9/2015 | Holmes |
| 9,234,204 B2 | 1/2016 | Qvit-Raz et al. |
| 9,288,981 B2 | 3/2016 | Gandhi et al. |
| 10,022,457 B2 | 7/2018 | Peyman et al. |
| 10,086,018 B2 | 10/2018 | Kovarik |
| 2003/0031737 A1 | 2/2003 | Rosenbloom |
| 2003/0124178 A1 | 7/2003 | Haley |
| 2003/0206995 A1 | 11/2003 | Bowling et al. |
| 2004/0053352 A1 | 3/2004 | Ouyang et al. |
| 2004/0096569 A1 | 5/2004 | Iow et al. |
| 2004/0115223 A1 | 6/2004 | Follansbee |
| 2004/0120991 A1 | 6/2004 | Gardner et al. |
| 2004/0136923 A1 | 7/2004 | Davidson |
| 2004/0142463 A1 | 7/2004 | Walker et al. |
| 2004/0166501 A1 | 8/2004 | Azimzai et al. |
| 2004/0228804 A1 | 11/2004 | Jones et al. |
| 2005/0118655 A1 | 6/2005 | Weinstock et al. |
| 2005/0196358 A1 | 9/2005 | Georglades et al. |
| 2006/0035008 A1 | 2/2006 | Virgallito et al. |
| 2006/0204591 A1 | 9/2006 | Burrell |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0207955 A1 | 9/2007 | Tanihara et al. |
| 2007/0218114 A1 | 9/2007 | Sorousch |
| 2007/0231923 A1 | 10/2007 | Cumberland et al. |
| 2007/0293587 A1 | 12/2007 | Haley |
| 2008/0112983 A1 | 5/2008 | Bufe et al. |
| 2008/0267933 A1 | 10/2008 | Ohlson et al. |
| 2008/0305089 A1 | 12/2008 | Bufe et al. |
| 2009/0196907 A1 | 8/2009 | Bunick |
| 2009/0196908 A1 | 8/2009 | Lee |
| 2009/0205083 A1 | 8/2009 | Gupta et al. |
| 2010/0029832 A1 | 2/2010 | Pinnavaia et al. |
| 2010/0260720 A1 | 10/2010 | Sprenger |
| 2010/0285098 A1 | 11/2010 | Haley |
| 2011/0142942 A1 | 6/2011 | Schobel et al. |
| 2011/0217368 A1 | 9/2011 | Prakash et al. |
| 2012/0027786 A1 | 2/2012 | Gupta |
| 2012/0029832 A1 | 2/2012 | Dodgson |
| 2012/0039806 A1 | 2/2012 | Lahoud et al. |
| 2012/0058094 A1 | 3/2012 | Blasser et al. |
| 2012/0128597 A1 | 5/2012 | Peters et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0059815 A1 | 3/2013 | Fournell et al. |
| 2013/0157876 A1 | 6/2013 | Lynch et al. |
| 2013/0259834 A1 | 10/2013 | Klaenhammer et al. |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0330215 A1 | 12/2013 | Li |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0199266 A1 | 7/2014 | Park |
| 2014/0238411 A1 | 8/2014 | Kovarik |
| 2014/0255351 A1 | 9/2014 | Berstad et al. |
| 2014/0271867 A1 | 9/2014 | Myers |
| 2014/0333003 A1 | 11/2014 | Allen |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0150792 A1 | 6/2015 | Klingman |
| 2015/0166641 A1 | 6/2015 | Goodman |
| 2015/0190435 A1 | 7/2015 | Henn et al. |
| 2015/0216917 A1 | 8/2015 | Jones |
| 2015/0252358 A1 | 9/2015 | Maeder |
| 2015/0329555 A1 | 11/2015 | Liras |
| 2015/0329875 A1 | 11/2015 | Gregory |
| 2015/0352023 A1 | 12/2015 | Berg |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0000838 A1* | 1/2016 | Harmsen ................ A61K 35/74 424/93.3 |
| 2016/0008412 A1 | 1/2016 | Putaala et al. |
| 2016/0040216 A1 | 2/2016 | Wilder |
| 2016/0089315 A1 | 3/2016 | Kleinberg et al. |
| 2016/0089405 A1 | 3/2016 | Lue |
| 2016/0151427 A1 | 6/2016 | Whitlock et al. |
| 2016/0168594 A1 | 6/2016 | Zhang et al. |
| 2016/0206564 A1 | 7/2016 | Trachtman |
| 2016/0206666 A1 | 7/2016 | Falb |
| 2016/0271189 A1 | 9/2016 | Cutcliffe |
| 2016/0314281 A1 | 10/2016 | Apte |
| 2016/0333348 A1 | 11/2016 | Clube et al. |
| 2017/0067065 A1 | 3/2017 | Falb et al. |
| 2018/0258411 A1 | 9/2018 | Kadiyala et al. |

* cited by examiner

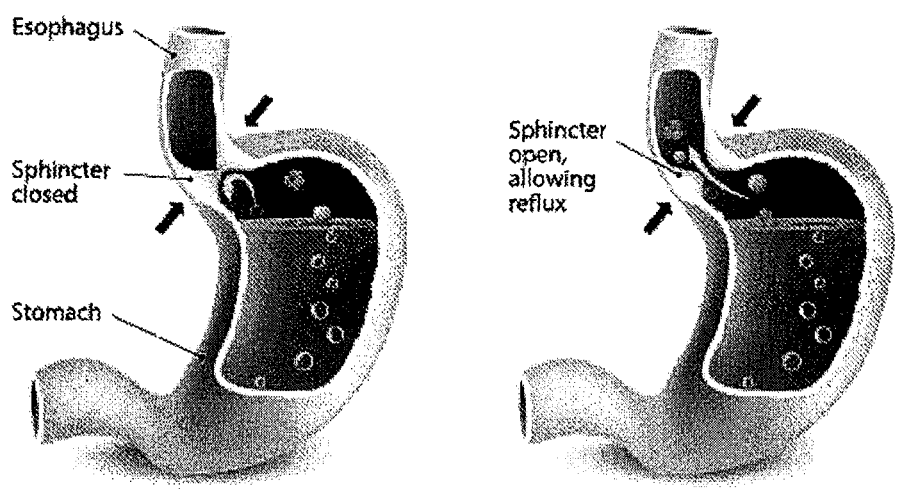

METHOD AND SYSTEM FOR REDUCING THE LIKELIHOOD OF COLORECTAL CANCER IN A HUMAN BEING

RELATED APPLICATIONS

This application is a continuation-in-part of U.S. patent application Ser. No. 15/395,419, filed Dec. 3, 2016 (now U.S. patent Ser. No. 10/086,018, issued Oct. 2, 2018), which is a non-provisional of U.S. Provisional Patent Application Ser. No. 62/274,550, filed on Jan. 4, 2016.

This application is a continuation-in-part application of U.S. patent application Ser. No. 14/752,192 filed Jun. 26, 2015 (now U.S. Pat. No. 9,549,842, issued Jan. 24, 2017), which is a continuation-in-part application of U.S. patent application Ser. No. 14/225,503 filed Mar. 26, 2014, (now issued U.S. Pat. No. 9,445,936, issued Sep. 20, 2016), which is a continuation of U.S. patent application Ser. No. 13/367,052, filed Feb. 6, 2012 (now issued U.S. Pat. No. 8,701,671, issuing on Apr. 22, 2014), which claims priority of U.S. Provisional Patent Application Ser. No. 61/439,652, filed on Feb. 4, 2011 and U.S. Provisional Patent Application Ser. No. 61/556,023, filed on Nov. 4, 2011.

This application also is a continuation-in-part application of U.S. patent application Ser. No. 15/270,034, filed Sep. 20, 2016 (now U.S. Pat. No. 9,750,802, issued Sep. 5, 2017), which is a continuation-in-part application of U.S. patent application Ser. No. 14/954,074, filed on Nov. 30, 2015 (now issued U.S. Pat. No. 9,457,077, issuing on Oct. 4, 2016), which is a continuation-in-part application of U.S. patent application Ser. No. 14/574,517, filed on Dec. 18, 2014 (now issued U.S. Pat. No. 9,408,880, issuing on Aug. 9, 2016), which claims priority of U.S. Provisional Patent Application Ser. Nos. 62/072,476, filed on Oct. 30, 2014; 62/053,926, filed on Sep. 23, 2014; 62/014,855, filed on Jun. 20, 2014; and 61/919,297, filed on Dec. 20, 2013.

This application is also a continuation-in-part application of U.S. patent application Ser. No. 15/228,454, filed Aug. 4, 2016 (now U.S. Pat. No. 9,585,920, issued Mar. 7, 2017).

This application claims priority of U.S. Provisional Patent Application Ser. No. 62/275,341 filed Jan. 6, 2016.

This application is also a continuation-in-part application of U.S. patent application Ser. No. 14/611,458, filed Feb. 2, 2015, which is a continuation-in-part application of U.S. patent application Ser. No. 14/502,097, filed Sep. 30, 2014 (now issued U.S. Pat. No. 9,010,340, issuing on Apr. 21, 2015), which is a continuation of U.S. patent application Ser. No. 14/307,651, filed on Jun. 18, 2014 (now issued U.S. Pat. No. 8,936,030, issuing Jan. 20, 2015), which is a continuation-in-part application of U.S. patent application Ser. No. 14/079,054, filed Nov. 13, 2013 (now issued U.S. Pat. No. 8,757,173, issuing on Jun. 24, 2014), which is a continuation of U.S. patent application Ser. No. 13/425,913. filed Mar. 21, 2012 (now issued U.S. Pat. No. 8,584,685, issuing on Nov. 19, 2013), and claims priority of U.S. Provisional Patent Application Ser. No. 61/467,767, filed Mar. 25, 2011.

The entire disclosure of the prior applications are considered to be part of the disclosure of the accompanying application and are hereby incorporated by reference.

FIELD OF THE INVENTION

A method for reducing the likelihood of colorectal cancer in an individual human being involves substantially reducing the human being's resident populations of gut microbes prior to administering a therapeutically effective amount of a bacterial formulation comprising *Faecalibacterium prausnitzii*, providing fructan fiber inulin in an amount sufficient to reduce the pH in the colon of the human being, and acidifying of the colon to enhance intestinal $Ma^{2+}$ absorption by the human being. Some embodiments include a step of administering a therapeutically effective amount of a bacterial composition comprising *F. prausnitzii* adapted to produce butyrate, wherein the *F. prausnitzii* has been modified via a clustered regularly interspaced short palindromic repeats (CRISPR) CRISPR associated protein (Cas) system to produce butyrate.

BACKGROUND OF THE INVENTION

Gastro-Esophageal Reflux Disease (GERD) is a chronic heartburn/stomach acidity affliction characterized by a series of symptoms including heartburn, chronic indigestion (dyspepsia), pyrosis, abdominal pain and swelling, epigastric pain, nausea, regurgitation, premature feeling of satiety, acid reflux coughing, vomiting and gas indigestion. GERD is a disease that mainly consists of abnormal refluxing of gastric contents into the esophagus through the lower esophageal sphincter, the lowest portion of the esophagus where it joins the stomach, which prevents the reverse passage of gastric content. The pH of the gastric content is acid, which is why the feeling of heartburn is produced and when it reaches the throat or the mouth, the taste is acidic and bitter, a symptom known as pyrosis. GERD is presently the most prevalent disease in the upper digestive system, and it is very prevalent in the Western world. It is estimated that at least 30 million patients suffer one of the aforementioned forms of GERD in the US each year, with the number rising significantly every year. The greatest incidence occurs in adults over forty. *H. pylori* is a gram-negative, slowly growing bacteria strain adapted to microaerophilic environments and its presence in the stomach is directly associated with various gastric diseases. 75% of gastric cancers are associated *H. pylori* infection.

Since *Helicobacter pylori* (initially called *campylobacter*) was discovered in 1980, it has been considered as a major cause in the pathogenesis of gastric ulcer, mucosa-associated lymphoid tissue (MALT) lymphomas, and gastric cancer. Eventually antibiotics were designed to eradicate this bacterium, which not only prevent peptic ulcer recurrence but also decrease the chances of developing gastric cancer. Around 50% of the world's human population is infected with *Helicobacter pylori*, a class I carcinogen. Eradication of *H. pylori* results in healing of gastric ulcer and may also reduce the incidence of gastric carcinoma. While various drug regimens have been used for the eradication of *H. pylori* such as triple or quadruple drug therapy, there has been an alarming increase in the resistance to antibiotics.

*Helicobacter pylori* can cause a chronic low-level inflammation of your stomach lining and is a major factor in the symptoms of acid reflux. Colonization of the human stomach by *Helicobacter pylori* and its role in causing gastric cancer is one of the richest examples of a complex relationship among human cells, microbes, and their environment. It is also a puzzle of enormous medical importance given the incidence and lethality of gastric cancer worldwide. There is a long felt but unsolved need to address GERD in a fashion that avoids the over administration of antibiotics, leading to increased antibiotic resistance.

Proton pump inhibitors (PPI's) work by blocking the production of acid in the stomach. In response, the body reacts by overcompensating, often revving up production of acid-making cells. Thus, one problem involved in attempting the cessation of PPI's is that individuals experience excess growth of acid producing cells in the stomach, so that when they unblock production of acid by stopping PPI doses, they have more of the acid-making cells, thus creating more acid production than they had previously experienced. The widespread treatment of GERD has also failed to reduce the incidence of esophageal cancers, with esophageal adenocarcinomas, which are associated with GERD, increasing by 350 percent since 1970. Thus, when people take PPI's, they do not cure the problem of reflux—but rather, they have just controlled the symptoms.

Stomach acid is needed to break down food and absorb nutrients, as well as for proper functioning of the gallbladder and pancreas. Taking PPI's changes the ecology of the gut and actually allows overgrowth of some things that normally would be kept under control. Long-term of use of PPI's may interfere with these processes and suppression of stomach acid, which kills bacteria and other microbes, may make people more susceptible to infections, like *C. difficile*, which can make one more susceptible to a dangerous infection marked by diarrhea, abdominal pain and even death.

*C. difficile* kills an estimated 14,000 to 30,000 people a year in the United States. Evidence of the link between *C. difficile* and PPIs was sufficiently strong that the Federal Drug Administration has issued alerts that PPI's may be causing a 65 percent increase in *C. difficile*-related diarrhea, that they may potentially lower magnesium levels—a condition that can cause muscle spasms, irregular heartbeat and seizures—and that they increase the risk of hip, wrist and spine fractures.

*Clostridium difficile* is a Gram-positive, strictly anaerobic, spore-forming bacterium found in mammalian intestinal tracts. *C. difficile* is one of the key public health problems in industrialized countries and one of the major nosocomial enteropathogens. *C. difficile*-associated diarrhea is currently the most frequently occurring nosocomial diarrhea worldwide. Two major risk factors for contracting *C. difficile* infections are the age of the individual and exposure to antibiotics. Antibiotic therapy causes alterations in the colonic microflora, allowing the development of *C. difficile* from preexisting or acquired spores. The pathogen synthesizes two major toxins, TcdA and TcdB, which glucosylate host GTPases, resulting in alterations in the enterocyte cytoskeleton. This induces intestinal cell lysis and inflammation, resulting in diarrhea, pseudomembranous colitis, and even death.

The long-term use of Prilosec and other proton-pump-inhibiting drugs is raising concerns as to the safety and wisdom of such long-term drug use as it invariably has consequences with respect to human health. PPI's are the third highest-selling class of drugs in the United States, with more than 100 million prescriptions and over $15 billion in sales. Some consider the long term use of proton pump inhibitors like Prevacid and Prilosec and the H2 blocker agents like Tagament, Pepcid, and Zantac to be dangerous. Such drugs significantly reduce the amount of acid available to digest food and the reduction of acid in the stomach also diminishes a primary defense mechanism for food borne infections, thus leading to an increased risk of risk of food poisoning.

Long-term use of PPI's can make it difficult to absorb some nutrients. Rebound acid hypersecretion, defined as an increase in gastric acid secretion above pre-treatment levels following antisecretory therapy, has been observed within two weeks after withdrawal of treatment and can lead to acid-related symptoms and possibly PPI dependency. Individuals have attempted to wean themselves off of these drugs gradually or else they experience a severe rebound of symptoms, often resulting in the problem being worse than it was before they started taking the medication. Emerging evidence suggests that PPIs are not as benign as once thought, with newer data implicating a potential association of PPIs with an increased risk of respiratory tract infections, gastrointestinal infections, bone fractures, hypomagnesemia, and the occurrence of rebound hyperacidity after discontinuation of PPI therapy.

In recent years, there have been numerous warnings about long-term use and high doses of PPI's being associated with an increased risk of bone fractures and infection with a bacterium called *Clostridium difficile* that can be especially dangerous to elderly patients. Studies have shown long-term PPI use may reduce the absorption of important nutrients, vitamins and minerals, including magnesium, calcium and vitamin B12, and might reduce the effectiveness of other medications, with the F.D.A. warning that taking Prilosec together with the anticlotting agent clopidogrel (Plavix) can weaken the protective effect (of clopidogrel) for heart patients. PPIH is the consequence of intestinal $Mg^{2+}$ malabsorption. An underappreciated aspect of PPIH is frequent secondary electrolyte disturbances such as hypocalcemia and hypokalemia. The clinical significance of reduced calcium ($Ca^{2+}$) levels is emphasized by several dozens of studies showing increased risk of bone fractures after chronic PPI use. Omeprazole inhibits passive paracellular $Mg^{2+}$ fluxes, predominantly present in the small intestine and omeprazole directly interferes with important transcellular $Mg^{2+}$ transport mechanisms of the colon.

The human gut harbors one of the most complex and abundant ecosystems colonized by more than 100 trillion microorganisms. Firmicutes and Bacteroidetes represent more than 90% of the relative abundance of the gut microbiome. The phylum Bacteroidetes is composed of Gram-negative, non-spore forming anaerobic bacteria that tolerate the presence of oxygen but cannot use it for growth. Actinobacteria (e.g., *Bifidobacterium*) are Gram-positive, multiple branching rods, non-motile, non-spore-forming, and anaerobic bacteria. The most abundant genera from the Bacteroidetes phylum are *Bacteroides* and *Prevotella* species. As the gut is an anaerobic environment, aerobic pathogenic species cannot invade and colonize it, but anaerobic and facultative pathogenic species can nevertheless invade it, causing diseases. High diversity defines healthy human gut microbiomes, whereas reduction in diversity is associated with dysbiosis—referring to an imbalance in the microbiome structure that results from an abnormal ratio of commensal and pathogenic bacterial species.

There is therefore a long felt but unsolved need for effective methods and compositions to reduce the likelihood of GERD and in treating, mitigating and preventing GERD, especially in concert with the widespread use of PPI's.

SUMMARY OF THE INVENTION

Humans possess an inflammatory response—the triggering of the overproduction of hydrochloric acid—as the stomach's primary response to bacterial colonization. Inflammation of the stomach lining coincides with production of peptides called cytokines, which stimulate production of a hormone called gastrin. Gastrin triggers parietal cells in the stomach lining to produce more hydrochloric acid, which kills off most invading microbes. Notably, *H. pylori* is the only bacterial organism in the stomach that cannot be killed by hydrochloric acid. If you inhibit gastric acid production, you interfere with the stomach's natural defense mechanism. An abnormally low level of acidity in the stomach is a factor in various disease states. Since reduced gastric acidity does appear to make the mammalian stomach more vulnerable to bacterial invasion and gastritis, however, physicians are advised to re-evaluate the long-term use of proton-pump-inhibiting drugs in their patients.

One aspect of the several embodiments of the present invention is directed to the modification of microbes in a manner that reduces, if not eliminates, the symptoms of GERD. *Helicobacter pylori* is one of several pathogens that persist within the host despite a robust immune response. *H. pylori* elicits a proinflammatory response from host epithelia, resulting in the recruitment of immune cells which manifests as gastritis. Certain embodiments employ CRISPR-Cas or Cpf1 systems to render *H. pylori* more susceptible to certain drugs, including antibiotics, thus addressing the resistance otherwise experienced by treating *H. pylori* with antibiotics.

While not bound by theory, it is believed that *H. pylori* survives antimicrobials, including calprotectin (CP), which employs nutrient sequestration, through alteration of its outer membrane. Thus, one embodiment of the present invention relates to the interference with and modification of the normal mechanism of *H. pylori* resistance to antibiotics by affecting the ability of *H. pylori* to form biofilms, including the retention and maintenance of lipid A production, which is normally interfered with by *H. pylori* when contacted by CP. In particular embodiments, CRISPR-Cas systems are employed to undermine the ability of *H. pylori* to form biofilms. One such strategy is to add additional genetic components in *H. pylori* cultures that include lipid A expression and the purposeful inclusion of such a culture of *H. pylori* in a person's stomach so as to establish a competitively beneficial culture of such modified *H. pylori* in the stomach. Thus, once such bacteria are the predominant bacteria, as compared to non-modified *H. pylori*, then the application of CP (or other suitable antibiotics) can be used to eliminate or vastly reduce the number of *H. pylori* bacteria in the person's stomach. Having the individual provided with further *H. pylori* cultures that possess such modified characteristics is further contemplated as a way in which to preclude the reestablishment of a wild type *H. pylori* culture from persisting in the person's stomach. By such a strategy, the person is able to substantially eradicate H. *Pylori* species that are resistant to antibiotics. Other ways to decrease the formation of *H. pylori* biofilms include increasing cell surface hydrophobicity. Another way is to enhance the function of the Lpx lipid A biosynthetic enzymes (e.g. LpxF, LpxL, and LpxR enzymes) to ensure that their functions are not perturbed. Thus, to combat *H. pylori* resistance to cationic antimicrobial peptides, one target is to affect the formation of biofilms and to reduce the ability of *H. pylori* to modify endotoxins. This can be achieved in various ways, but preferably by employment of CRISPR-Cas systems to interfere with genes involved in the formation of biofilms by *H. pylori*.

Certain embodiments are directed to the modification of resident *H. pylori* populations in vivo in a person's stomach so as to beneficially disrupt the colonization of the gastric glands by *H. pylori*. Other aspects involve the modification of dietary components and essential micronutrients in concert with the gastrointestinal microbiota to affect a beneficial modification of *H. pylori* activity so as to maintain it as a commensal bacteria and to prevent its activity as a pathogen, thus precluding its carcinogenic potential.

One aspect of the present invention is directed to therapeutic interventions in the microbiome directed against molecular entities, such as essential and antibiotic resistance genes to quorum sensing systems components used to control microbial networking behaviors, including the chemical communication and production of virulence factors. Various embodiments are focused on dietary interventions and microbial modification genetic tools to modify and/or eliminate pathogenic microorganisms and to control dysbiosis. Various embodiments of the present invention are also directed towards the modification of the human-microbiota ecosystem to promote health and to combat disease, including the modification and/or elimination of certain bacteria living in the human body. The determination of human microbiota and the analyses of the presence or absence of specific microbial species in accordance with particular diseases provides one of skill in the art with the ability to identify particular biomarkers and to target the same to treat GERD.

While phage therapy could potentially have beneficial impact on human microbiomes, host specificity greatly limits the types of bacteria that can be employed and the selection of a specific phage to use as a therapeutic agent requires in-depth knowledge of the pathogen causing a given disease. In the absence of such knowledge, some have suggested the use of a cocktail of different species of phages to broaden the range of action, but such a cocktail could have undesired negative effects on the microbial community. Thus, in preferred embodiments of the present invention, CRISPR systems are employed to effect desired microbial modifications. The relative simplicity of the mechanism of action and the peculiarities of Cas9 make the CRISPR/Cas9 system an ideal tool for a vast assortment of procedures, particularly for genomic editing, and in various embodiments of the present invention, the editing of bacterial strains is employed to interfere with the development of GERD and to otherwise treat GERD.

In various embodiments of the present invention, various targets for intervention using CRISPR-Cas systems include the modification of bacteria resident in the human gut that are distinct from humans in various respects. For example, most bacteria synthesize thiamine de novo, whereas humans depend on dietary uptake. Methionine is not synthesized de novo in humans and must be supplied by diet. In contrast, most bacteria need to synthesize methionine to survive. There are a myriad of other orthologous gene groups conserved in both human and human commensal gut microflora that are not suitable targets for drug development. The majority of unique targets found in microbes' genomes are genes responsible for the metabolism of carbohydrates, amino acids, xenobiotics, methanogenesis, and the biosynthesis of vitamins and isoprenoids, and in particular for the purposes of various embodiments of the present invention, focus is directed to those genes that are non-homologous to those encompassed in human genome. A number of microbial genes and products, including bacteriocins, lysins, holins, restriction/modification endonuclease systems, and other virulence factors contribute to resistance to antibiotics. Thus, an alternative to killing or inhibiting growth of pathogenic bacteria is targeting these key regulatory systems. Other aspects of the present invention are directed to targeted changes in microbiota by the rational use of prebiotics and probiotics to abolish metabolic alterations associated with various maladies, including GERD, obesity, cancer, etc.

In particular embodiments, compounds such as halogenated furanones produced by many microbial species, mostly belonging to the proteobacteria, are employed to interfere with AHL and AI-2 QS pathways in Gram-negative and Gram-positive bacteria. It is believed that by interrupting normal systems of bacterial inter and intra quorum sensing, one may effectively modify bacterial cell-cell communication in a manner that prevents colonization by pathogenic bacteria, and in particular, can be employed to interfere with biofilm formation by *H. pylori* and thus, treat GERD.

High doses and frequent use of antibiotics can disrupt and destabilize the normal bowel microbiota, predisposing patients to develop *Clostridium difficile* infections. Up to 35% of these patients develop a chronic recurrent pattern of disease. Fecal bacteriotherapy is the transplantation of liquid suspension of stool from a donor (usually a family member) and has been used successfully in severe cases of recurrent *C. difficile* relapse. Many problems exist with this therapy since it can increase the risks of transmitting other pathogens. One particular focus of the present invention is to employ transplanted microbiota to treat metabolic disorders in humans but that limit the risks involved in conventional fecal transplants. For example, via the use of modified bacteria (e.g. using CRISPR-Cas systems) one is able to more effectively employ antibiotics to target particular regions of the body, to target particular bacteria, etc. in a manner that avoids the complications experienced in the typical use of antibiotics, which cause complications from *C. difficile* growth.

In particular embodiments, probiotic microorganisms that possess resistance to low gastric pH and have the capacity to reach the intestines alive, are used to exert beneficial effects on the human body, preferably lactic acid-producing bacteria of the *Lactobacillus* and *Bifidobacterium* genera. Such microorganisms are preferably those modified using CRISPR-Cas to provide a population that can be more easily controlled and manipulated to maintain particular levels in an individual's microbiome. Specifically, some embodiments of the present invention include regulating the balance of intestinal microbiota by physically blocking the adhesion of pathogenic species onto epithelial cells, such blocking action directly mediated by means of increases in the production of a mucosal barrier by goblet epithelial cells and/or by regulating epithelial permeability by enhancing the formation of tight-junctions between cells. Use of CRISPR-Cas to modify or delete virulence factors of particular bacteria, such as adhesion abilities thereof, is employed in this fashion.

In various embodiments of the present invention, CRISPR/Cas9 is used to selectively deplete a given bacterial community of a particular harmful strain or species, or of particular virulence factors possessed by particular strains of bacteria. Thus, in certain embodiments, the identification of a harmful pathogen is performed, and CRISPR/Cas9 is then used to selectively deplete or modify that particular bacterial species from an individual's gut microbiota. The use of antibiotics is believed to increase the ability of bacteria to acquire drug resistance-encoding plasmids. Thus, the CRISPR/Cas9 system may be used to introduce specific mutations into essential, antibiotic resistance and virulence genes, as well as to directly modulate the expression of particular genes. For example, one can employ a Cas protein that lacks nuclease activity but retains a binding capacity so as to repress bacterial transcription by binding to promoter regions to effect the blocking of transcriptional initiation and/or elongation. CRISPR-Cas or Cpf1 systems may also be used to fuse regulatory domains in order to switch on/off the expression of specific genes. Thus, the present invention includes the engineering of commensal bacteria with improved properties using a CRISPR/Cas system to prevent and treat diseases. One of skill in the art will appreciate the steps required to affect the desired levels of target specificity and delivering efficiency.

Still other embodiments employ the modification of various beneficial bacteria so that they express certain compounds and substances, notably those substances found to be effective as an anti-*H. pylori* agent, such as those isolated from garlic and ginseng. Alliin, the main active molecule present in Garlic extract, is used to effect immune modulation. The use of dialkyl-thiosulfinate and/or propy thiosulfonate can be employed to improve disease resistance of a pathogen, with these compounds generated from the natural degradation of propiin, a molecule present in most *Allium* species, and more specifically onion, shallots or chives. Still other sulfur compounds can may be employed to inhibit *H. pylori* colonization. Using CRISPR-Cas, one is able to modify resident bacteria to express the active ingredient in garlic found to be an effective killer of *H pylori*. Such expressed compounds include those described above.

Similarly, another aspect of the present invention is to control *H. pylori* populations in an individual's stomach by a diet including kimchi. Other aspects are directed to the expression of kimchi genes by one or more bacterial species that reside in a human stomach. In a manner similar to the expression of certain genes derived from garlic, one is therefore able to control the population of *H. pylori* in a person's stomach. The use of CRISPR-Cas to insert genes into particular bacteria so as to facilitate the control of *H. pylori* is one aspect of certain embodiments, including the insertion of genes having the active agent contained in Korean kimchi and garlic. The incidence of gastric cancer is about 20 per 100,000 population (in Korea) and about 50 per 100,000 population (in Japan, where far less kimchi is eaten), demonstrating that kimchi is effective as a cancer preventative agent. Similarly, the expression of garlic related genes by one or more bacterial species that reside in a human stomach is another embodiment of the present invention. The use of garlic (as well as kimchi) to address GERD is considered to be a teaching away from the prior art, as many have identified garlic and onions as causing heartburn. Garlic (*allium sativum*), like onions, shallots and leeks, among others, belongs to the alliaceae family, and all contain organosulfur products. Garlic in particular contains allicin, an organosulfur compound that is produced when garlic is broken or crushed, through the action of the allinase enzyme on alliin. Allicin is a potent phytocide, with marked antibiotic and antifungal properties. The release of allicin produces other sulfur derivatives, such as ajoene, allyl sulfides, diallyl sulfides, allyl methyl disulfide, allyl methyl trisulfide, s-allyl cysteine and diallyl trisulfide. Allicin pronouncedly inhibits the secretion of various cytokines (IL-1b, IL-8, IP-10 and MIG) from epithelial cells, suppressing the expression of interleukin 8 (1-8) and interleukin 1b (IL-1b) mRN and is therefore considered to be effective in attenuating intestinal inflammation. It is believed that low doses of garlic oil suppresses NOS (inducible Notric Oxide Synthase) activity, ulceration and apoptosis of the intestinal mucosa. At high doses, however, garlic oil has shown a toxic effect, which is why it is deduced that garlic is beneficial in moderate doses, but can be toxic in high doses. Garlic extracts and garlic oil have also been found to be powerfully anti-microbial against other GI bacteria such as *Escherichia coli, Shigella* sp, *Salmonella* sp, and *Proteus mirabilis*.

One aspect of the present invention is directed to the use of probiotics to modulate the human microbiota and promote health and prevent antibiotic side effects. L. species are acid-resistant and commensal and their concentrations in the normal human stomach vary between 0 and $10^3$ mL$^{-1}$. They can survive in the stomach for periods of up to 2 h. In various embodiments, fructo-oligosaccharides (FOS) and trans-galacto-oligosaccharides (TOS), such as inulin, are used to selectively stimulate growth and activity of health-promoting bacteria. In this regard, dietary inulin fibers are used to stimulate Mg$^{2+}$ and Ca$^{2+}$ absorption and are a potent stimulant of mineral absorption, especially achieved by oligofructose-enriched inulin. Certain strains of gut bacteria have a preference for inulin fibers. Thus, one aspect of the present invention is to selectively advance the population of such bacteria in a person's gut. It is known that N-butyric acid increases Ca$^{2+}$ and Mg$^{2+}$ absorption. Thus, certain embodiments of the present invention are directed to the provision of bacteria designed to produce n-butyric acid to treat PPI-induced Ca$^{2+}$ disturbances. It is believed that dietary inulin stimulates intestinal Mg$^{2+}$ absorption, and thus, other embodiments of the present method include the provision of dietary inulin in addition to the provision of the various bacteria strains as described herein. One aspect of the present invention is therefore directed to the impact of PPIs on Ca$^{2+}$ homeostasis and provides a treatment for PPI-induced mineral disturbances. Dietary oligofructose enriched inulin fibers are believed to prevent omeprazole-induced reduction of Ca$^{2+}$ absorption and lead to improved intestinal Mg$^{2+}$ absorption, thus preventing PPI-induced mineral deficits in individuals.

In various embodiments, the present invention is directed to the use of dietary inulin to counteract reduced intestinal Ca$^{2+}$ absorption upon PPI treatment. One aspect of the present invention is directed to the local luminal acidification of the colon to enhance intestinal Mg$^{2+}$ absorption and by so doing, preventing PPIH. Other embodiments are directed to the use of the fructan fiber inulin to reduce intestinal pH, such ingested inulin fibers being fermented in the large intestine by bifidogenic gut bacteria, resulting in short-chain fatty acids (SCFA), which in turn acidify the colon. Thus, one aspect of various embodiments is directed to the stimulating action of SCFA on intestinal Mg$^{2+}$ absorption by reducing the luminal pH. Certain aspects are directed to the enhancement of intestinal Mg$^{2+}$ and Ca$^{2+}$ absorption in order to counteract omeprazole-induced defects in mineral uptake. Proton-pump inhibitor-induced hypomagnesemia (PPIH) is the most recognized side effect of proton-pump inhibitors (PPIs). Additionally, PPIH is associated with hypocalcemia and hypokalemia. It is hypothesized that PPIs reduce epithelial proton secretion and thereby increase the pH in the colon, which may explain the reduced absorption of and Mg$^{2+}$ and Ca$^{2+}$. Fermentation of dietary oligofructose-enriched inulin fibers by the microflora leads to acidification of the intestinal lumen and by this enhances mineral uptake. One aspect of the present invention is therefore directed to the improvement of mineral absorption by application of dietary inulin to counteract PPIH.

In various embodiments of the present invention, candidate probiotic strains are isolated from fecal samples, especially after enrichment with a prebiotic application. As described in other applications incorporated herein, the use of particular fecal samples from healthy Amish individuals is employed to combat GERD Moreover, one strategy for enhancing the establishment of probiotic bacteria in the human intestinal tract is via the parallel administration of a prebiotic. In vivo selection (IVS) may be employed to isolate candidate probiotic strains from fecal samples following enrichment with a prebiotic. For example, isolated bifidobacteria from human subjects who consumed increasing doses of galactooligosaccharides (GOS) revealed an 8-fold enrichment in *Bifidobacterium adolescentis* strain IVS-1. It is believed that such selected strains are able to outcompete resident *Bifidobacterium* populations. One aspect of the present invention, especially employing one or more of the modified bacteria as described herein, is to substantially enhance the establishment and competitiveness of one or more putative probiotic strains in an individual's gastrointestinal tract to combat GERD.

One aspect of the present invention is directed to the provision of pharmaceuticals based on an individual's own microbiome. Thus, in certain embodiments, isolation of particular bacteria from an individual's stool is employed and CRISPR-Cas and/or Cpf1 systems are then used to modify such bacteria in various beneficial ways, as described herein. The reintroduction of such modified bacteria into the person's gut (e.g. via fecal transplantation) provides a way to selectively and competitively compete with other undesired bacteria in the person's gut. Preferably, the resident populations of gut microbes are reduced substantially before the reintroduction of the modified bacteria, thus providing a better chance and opportunity for the establishment of a population of preferred bacteria, as modified via the CRISPR-Cas systems, as described herein.

The growth of microbiota communities is under control of distinct subfamilies of host genes encoding antimicrobial peptides (AMPs). When bacteria colonize a given human habitat, the expression of AMPs, including α and β defensins and cathelicidins, is upregulated in order to limit the spreading of bacteria. The equilibrium between the immune system and immunoregulatory functions of bacteria appears to be a delicate balance in which the loss of a specific species can lead to an overreaction or suppression of the innate immune system. The maintenance of a stable, fermentative gut microbiota requires diets rich in whole plant foods particularly high in dietary fibers and polyphenols. Individuals colonized by bacteria of the genera *Faecalibacterium, Bifidobacterium, Lactobacillus, Coprococcus*, and *Methanobrevibacter* have significantly less of a tendency to develop obesity-related diseases like type-2-diabetes and ischemic cardiovascular disorders. These species are characterized by high production of lactate, propionate and butyrate as well as higher hydrogen production rates, which are known to inhibit biofilm formation and activity of pathogens. Thus, in various embodiments of the present invention, these bacterial species are selected and administered to an individual in preferred ratios that reflect those of healthy individuals so as to attain the general balance of bacterial populations in a person's gut. Moreover, preferably bacteria are selected that are effective in inhibiting biofilm formation and in particular, those that demonstrate a high production of lactate, propionate, butyrate and hydrogen. CRISPR-Cas and/or Cpf1 may be employed to provide such characteristics to the selected bacterial species in this regard.

CDT (*Clostridium difficile* transferase) is a binary, actin ADP-ribosylating toxin frequently associated with hypervirulent strains of the human enteric pathogen *C. difficile*, the most serious cause of antibiotic-associated diarrhea and pseudomembranous colitis. CDT leads to the collapse of the actin cytoskeleton and, eventually, to cell death. The lipolysis-stimulated lipoprotein receptor (LSR) is the host cell receptor for CDT. By applying the CRISPR-Cas technology to interfere with the binding component of CDT, preferably by impacting amino acids 757 to 866 of CDT, one is able to interfere with the binding of CDT to the LSR. Thus, interfering with the interaction between CDT and its receptor LSR, is one way to provide an anti-toxin strategy for preventing cell entry of the toxin. Use of the active expression of CRISPR arrays in *C. difficile* strains is therefore one way in which to counter *Clostridium difficile* nosocomial infections associated with antibiotic therapies. One aspect of certain embodiments is directed to modifying the site where the bacterium *Clostridium difficile*'s binary toxin binds to intestinal cells' LSR (lipolysis-stimulated lipoprotein receptor) protein and triggers a mechanism that results in the invasion of the host cells by the bacteria. *Clostridium difficile* produces the binary, actin ADP-ribosylating toxin CDT (*Clostridium difficile* transferase). While CDT can lead to death of the host cells through collapse of the actin cytoskeleton, low doses of CDT result in the formation of microtubule-based protrusions on the cell surface that increase the adherence and colonization of *C. difficile*. Thus, one aspect of certain embodiments relates to the interference with the adherence characteristics of this bacteria by reducing the amount of CDT produced by bacterial cells, thus providing a population of *C. difficile* that do not pose the problems of wild type strains. One aspect of certain embodiments involves blocking certain areas in the toxin and the receptor in order to prevent the *Clostridium difficile* transferase toxin from entering the host cell.

Other embodiments are directed to a system and method for reducing the likelihood of GERD and includes the modification of an individual's gut microbes in a manner that reduces, if not eliminates, the symptoms of GERD. Certain embodiments employ CRISPR-Cas or Cpf1 systems to render H. Pylori more susceptible to certain drugs, including antibiotics, thus addressing the antibiotic resistance otherwise experienced by treating H. Pylori with antibiotics.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications.

BRIEF SUMMARY OF THE DRAWINGS

FIG. 1 illustrates a normal stomach as compared to a GERD stomach, showing that the sphincter is closed in a normal stomach, whereas the sphincter is open in a GERD stomach, thus permitting reflux to occur.

DETAILED DESCRIPTION OF CERTAIN EMBODIMENTS OF THE PRESENT INVENTION

In various embodiments of the present invention, bacterial species to be exposed to a person's gut microbiome, include those specifically modified by employing the CRISPR-Cas and CRISPR-Cpf1 systems to render the virulence factors of various bacteria ineffective. CRISPR (Clustered Regularly Interspaced Short Palindromic Repeats) is a prokaryotic adaptive defense system that provides resistance against alien replicons such as viruses and plasmids. CRISPRs evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complimentary to the viral genome, mediates targeting of a Cas9 protein to a target sequence in the viral genome. The Cas9 protein cleaves and thereby silences the viral target. In preferred embodiments, rather than using CRISPR-Cas, one employs the CRISPR-associated endonuclease Cpf1. e.g. a CRISPR from *Prevotella* and *Francisella* 1 (Cpf1) nuclease for CRISPR-based genome editing.

CRISPR-Cpf1, a class II CRISPR effector that is distinct from Cas9, is a single RNA-guided endonuclease that uses T-rich PAMs and generates staggered DNA doublestranded breaks instead of blunt ends. Its smaller protein size and single RNA guide requirement makes CRISPR applications simpler and with more precise control.

In some preferred embodiments, the present invention provides methods for the use of CRISPR loci to determine the potential virulence of a phage against a cell and the use of CRISPR-cas to modulate the genetic sequence of a phage for increased virulence level.

Certain embodiments of the present invention are directed to the interplay between periodontitis and GERD, with the belief that the oral microbiome and the microbiome of an individual's stomach and gut are related and affect the overall health of the individual, including but not limited to the occurrence of GERD. Thus, various embodiments of the present invention are directed to a method for protecting a person from periodontitis and related illnesses associated therewith involving generating a bacterial oral microbiome culture comprising *T. denticola* and/or *Prevotella* bacteria modified by employing CRISPR-Cas or Cpf1 comprising the steps of: (a) exposing a parent bacterial strain of one of c *T. denticola* and/or *Prevotella* comprising at least a portion of a CRISPR locus to at least one bacteriophage to produce a mixture of bacteria comprising at least one bacteriophage resistant variant strain comprising a modified CRISPR locus comprising at least one additional spacer in said modified CRISPR locus; (b) exposing a parent bacterial strain comprising at least a portion of a CRISPR locus, different to the parent bacterial strain of step (a), to a different at least one bacteriophage to that of step (a) to produce a mixture of bacteria comprising at least another bacteriophage resistant variant strain comprising a modified CRISPR locus comprising at least one additional spacer in said modified CRISPR locus; (c) selecting said bacteriophage resistant variant strains from said mixtures of bacteria; (d) selecting said bacteriophage resistant variant strains comprising an additional spacer in said modified CRISPR locus from said bacteriophage resistant strains selected in step (c); and (e) isolating said bacteriophage resistant variant strains, wherein said strains comprise an additional spacer in said modified CRISPR locus.

Spacers in a CRISPR cassette confer immunity against viruses and plasmids containing regions complementary to the spacers and hence, they retain a footprint of interactions between prokaryotes and their viruses in individual strains and ecosystems. The human gut is a rich habitat populated by numerous microorganisms, each having a CRISPR system. To comply with written description and enablement requirements, incorporated herein by the following references are the following patent publications: 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 2015/0132263 to Liu; and 2014/0068797 to Doudna; 2014/0255351 to Berstad et al.; 2015/0086581 to Li; PCT/US2014/036849 and WO 2013026000 to Bryan.

The CRISPR-Cas system may also be employed to render certain bacteria sensitized to certain antibiotics such that specific chemical agents can selectively choose those bacteria more susceptible to antibiotics, see, e.g. US Pat. Publication No. 2013/0315869 to Qimron, which is incorporated in its entirety by this reference.

The microbiome of an individual is disrupted by antibiotics and thus, the employment of CRISPR as a way to bypass common modes of multidrug resistance, while being selective for individual strains, is employed in various embodiments of the present invention to attain the benefits derived by the presence of particular bacteria.

Another aspect of certain embodiments includes making synthetic CRISPR-containing RNAs that target genes of interest and using them with Cas enzymes. The specificity of CRISPR-Cas systems permits one to design methods to target a single bacterial species so that only essential genes form that one species is targeted and cut up. CRISPR-Cas systems are employed in various ways in the many embodiments of the present invention to retain the beneficial bacterial communities intact and to offer protection against undesired bacterial pathogens.

CRISPR has a certain protein in it called Cas9 that acts like a scissor as it recognizes specific sequences of DNA and cuts it enabling one to perform genome-editing of a bacterial genome in a person's microbiome. There exists another CRISPR system, CRISPR-Cpf1 that is even more preferred for use in microbial systems.

Cpf1 is important in bacterial immunity and is well adapted to slice target DNAs. Cpf1 prefers a "TTN" PAM motif that is located 5' to its protospacer target—not 3', as per Cas9, making it distinct in having a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 merely requires a cRNA that is about 43 bases long—of which 24 nt is protospacer and 19 nt is the constitutive direct repeat sequence. In contrast, the single RNA that Cas9 needs is still ~100 nt long. Cpf1 is apparently directly responsible for cleaving the 43-base cRNAs apart from the primary transcript.

With respect to the cleavage sites on the target DNA, the cut sites are staggered by about 5 bases, thus creating "sticky overhangs" to facilitate gene editing via NHEJ-mediated-ligation of DNA fragments with matching ends. The cut sites are in the 3' end of the protospacer, distal to the 5' end where the PAM is. The cut positions usually follow the 18th base on the protospacer strand and the 23rd base on the complementary strand (the one that pairs to the crRNA). In Cpf1 there is a "seed" region close to the PAM in which single base substitutions completely prevent cleavage activity. Unlike the Cas9 CRISPR target, the cleavage sites and the seed region do not overlap. One advantage of the present invention, as compared to techniques that rely on CRISPR systems to modify mammalian cells, is that the system and method of preferred embodiments are directed to bacterial systems—rather than eukaryotic systems. It is believed that Cpf1 may be better than Cas9 for mediating insertions of DNA, namely because its guide RNA is only 43 bases long, making it feasible to purchase directly synthesized guide RNAs for Cpf1, with or without chemical modifications to enhance stability.

The CRISPR system may be employed in various embodiments to strengthen antibiotics or to kill the bacteria altogether. By removing the bacteria's genes that make them antibiotic-resistant, CRISPR can boost the effectiveness of existing drugs. CRISPR can also be used to remove a bacteria's genes that make them deadly and facilitate RNA-guided site-specific DNA cleavage. Analogous to the search function in modern word processors, Cas9 can be guided to specific locations within complex genomes by a short RNA search string.

In various embodiments, the CRISPR-Cas systems is employed to control the composition of the gut flora, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas systems. Because of the sequence specificity of targeting, CRISPR-Cas systems may be used to distinguish strains separated by only a few base pairs.

As described above, certain aspects of the present invention address the differences of *C. difficile* and other bacteria, especially with respect to the understanding that the CRISPR-Cas system in *C. difficile* is unique due to the presence of multiple active CRISPR arrays, which is in contrast to the presence of silent or barely expressed CRISPR loci in some other bacteria such as *Streptococcus pyogenes* and *E. coli*. In relation to the *C. difficile* infection cycle, stress conditions, including antibiotic treatments, induce prophages and lead to the release of phage particles and infection of neighboring bacteria, thus contributing to the CRISPR spreading within *C. difficile* populations. Together with dysbiosis, this can increase the rigor of this pathogen. Thus, employment of CRISPR-Cas to excise particular characteristics of *C. difficile* to defeat, for example, the ability to release phage particles, and to then provide such modified bacteria to a person's gut, thus maintaining the balance as referred to therein, is one way in which to modify a person's gut microbiota in a beneficial manner without the long term use of PPI's or antibiotics, thus avoiding the dangers and problems associated therewith.

The specificity of targeting with CRISPR RNAs may be employed to readily distinguish between highly similar strains in pure or mixed cultures. Thus, in certain embodiments, varying the collection of delivered CRISPR RNAs is employed to quantitatively control the relative number of individual strains within a mixed culture in a manner to circumvent multidrug resistance and to differentiate between pathogenic and beneficial microorganisms.

In certain other aspects, particular embodiments of the present invention are directed to the use of CRISPR to excise certain prior infectious virus DNA sequences that are considered responsible for the increased obesity of individuals harboring the same. Reference is made to Kovarik, U.S. Pat. No. 8,585,588, "Method and system for preventing virus-related obesity and obesity related diseases," incorporating the same by this reference. After determining whether one has been infected with a particular virus, the viral DNA can then be excised via CRISPR-Cas to remove the previously inserted DNA, thus effectively reducing if not eliminating the virus gene from the individual. Thereafter, to avoid being infected with such virus again, practice of the method as set forth in U.S. Pat. No. 8,585,588 will lessen, if not prevent, reacquisition of such virus.

Use of CRISPR-Cas provides a generalized and programmable strategy that can distinguish between closely related microorganisms and allows for fine control over the composition of a microbial population for use in the present invention. Thus, the RNA directed immune systems in bacteria and archaea (e.g. their CRISPR-Cas systems) is employed in various embodiments of the present invention to selectively and quantitatively remove and/or alter individual bacterial strains based on sequence information to enable the fine tuning of exposure of desired antigens. Thus, such genome targeting using CRISPR-Cas systems allows one to specifically remove and/or alter individual microbial species and strains in desired ways.

In various embodiments, it is desirable to remove—using CRISPR-Cas systems—particular viable genes in pathogenic bacteria and/or other pathogenic portions (e.g. plasmids, etc. of such bacteria)—while sparing other desired commensal bacteria, in order to provide exposure to desired immune developing proteins.

In various embodiments, one of skill in the art will appreciate that removal or alteration of particular strains of bacteria may be achieved using both type I and type II CRISPR-Cas systems, given the distinction between these systems being that type I systems cleave and degrade DNA through the action of a 3'-to-5' exonuclease, whereas type II systems only cleave DNA. In still other embodiments, multiple guide RNAs can also be used to target several genes at once. The use of effector fusions may also expand the variety of genome engineering modalities achievable using Cas9. For example, a variety of proteins or RNAs may be tethered to Cas9 or sgRNA to alter transcription states of specific genomic loci, monitor chromatin states, or even rearrange the three-dimensional organization of the genome.

There are ongoing ethical concerns arising with respect to the use of CRISPR-Cas systems—especially as it relates to modification of the human genome. Still others are concerned about the chain reactions possible if undesired gene expression is directed to insects (mosquitoes, etc.) or invasive species, etc.—such that as yet unknown problems may arise by the removal or alterations of problems presently experienced. In preferred embodiments of the present invention, however, such issues are much less prevalent for various reasons. First, because preferred embodiments relate to the modification of microbes—rather than to the human genome—and especially only those microbes that show tropism for humans, the unintended consequences of employing Crispr-Cas on organisms is lessened, if not eliminated. Moreover, use of CRISPR-Cas to also insert genes that have controllable elements such that the cells are killed by triggering the expression of such genes, is another way to reduce if not eliminate concerns about an unintended release of a modified organism. These types of controls are well known to those of skill in the art and have been long employed, for example, by those involved in creating genetically engineered organisms, such as by inserting genes so that organisms become susceptible to various conditions, such as temperature, antibiotic exposure, etc., such that microbes that may somehow escape desired conditions will not be viable.

On aspect of many embodiments of the present invention include the use of specialized viruses to supply CRISPR/Cas to rid bacteria of antibiotic-resistance plasmids and/or other virulence factors. Virulence factors of Gram-negative anaerobes such as *Prevotella* include, for example, fimbria, hemolysins, adhesions and hemagglutinins. These bacteria commonly produce immunoglobulin-degrading enzymes and some produce tissue-degrading enzymes. Additionally, bacteria of the genus *Prevotella* are often resistant to antibiotics, such as tetracycline, erythromycin, and β-lactam antibiotics. In practice, a *Prevotella*-targeting lambda phage is created that encodes the CRISPR genes plus spacers that target two conserved β lactamases, enzymes that confer resistance to β-lactam antibiotics. Once integrated into the *Prevotella* genome, the phage prevents the transfer of β lactamase-encoding plasmids and can also delete these plasmids from individual bacterial cells. These lambda phage-encoding bacteria then become sensitive to treatment with antibiotics.

In other embodiments, the use of CRISPR-Cas systems is employed to increase butyrate production of these bacteria. For example, *F. prausnitzii*, one of the most abundant species in the colon, is an important producer of butyrate, a major product of carbohydrate fermentation which is implicated in providing protection against colorectal cancer and ulcerative colitis.

Short-chain fatty acid production by commensal bacteria is important in regulating the immune system in the gut. Butyrate plays a direct role in inducing the differentiation of regulatory T cells and suppressing immune responses associated with inflammation. Butyrate is normally produced by microbial fermentation of dietary fiber and plays a central role in maintaining colonic epithelial cell homeostasis and barrier function.

Preferably, the modified bacteria employed in the present invention are administered orally to a patient in order to deliver the therapeutic directly to the site of inflammation in the gut. The advantage of this approach is that it avoids systemic administration of immunosuppressive drugs and delivers the therapeutic directly to the gastrointestinal tract. The viability and stability of such modified bacteria is enhanced to support the production of such microbes of desired agents, e.g. tomatidine, p53 protein, etc. and by doing so, a method is provided to reduce gut inflammation, enhance gut barrier function, and/or treat autoimmune disorders. Preferably, such modified bacteria are capable of producing therapeutic anti-inflammation and/or gut barrier enhancer molecules, particularly in the presence of reactive nitrogen species, and more preferably the bacteria are functionally silent until they reach an environment containing local RNS, wherein expression of the therapeutic molecule is induced. In certain embodiments, the genetically engineered bacteria are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate is produced, which induces the differentiation of regulatory T cells in the gut and/or promotes the barrier function of colonic epithelial cells. Use of such modified bacteria, especially those modified via CRISPR-cas systems, provides a way to generate a desired therapeutic effect in a manner that lowers the safety issues associated with systemic exposure.

Molecular mechanisms modulated by gut microbiota promote inflammation and support colorectal carcinogenesis. Both endogenous and exogenous miRNAs modulate tumor-related inflammation in colorectal cancer. Gut microbiota has an influence on colorectal carcinogenesis and the microbe population living in the human intestine plays a significant role in the development and progression of colorectal cancer. Maintenance of healthy of intestinal epithelia is critical to provide optimal nutrient absorption, as well as an efficient immune barrier. The balance between intestinal microbiota, intestinal epithelium and host immune system is decisive for normal functionality of the intestinal cells. Therefore, changes in any of these three factors may influence the functionality of the intestinal epithelium. The benefits of the body in relation to gut microbiota are related to extraction of the energy from the fermentation of undigested carbohydrates and from the absorption of short-chain fatty acids. Butyrate is the most important of these fatty acids being metabolized by the colonic epithelium and is the favorite energy source of colonocytes. The most important bacteria producing this fatty acid are *Faecalibacterium prausnitzii*, which belongs to the *Clostridium leptum* cluster, and *Eubacterium rectale/Roseburia* spp., which belong to the *Clostridium coccoides*. In healthy colonocytes, butyrate hampers apoptosis and further mucosal atrophy. In colorectal cancer cells, butyrate has been proven to stimulate differentiation, impede cell proliferation, lead to apoptosis and inhibit angiogenesis.

Butyrate protects human colon cells from DNA damage. In addition to butyrate, gut microbiota are also implicated in the constitution of another category of beneficial fatty acids, such as conjugated linoleic acids, having anti-inflammatory and cancer protective properties.

MicroRNA (miRNAs) are small (21-25 nucleotide) non-coding RNAs (ncRNAs) that regulate the translation and stability of their specific mRNA targets. The aberrant expression of microRNAs is related to the initiation and progression of various cancers, with MiRNAs acting as tumor suppressors or oncogenes. Inflammation determines changes in expression of miRNAs, primarily through the actions of proinflammatory cytokines. The role of miRNAs is believed to be in the initiation and progression of human cancer, as well as in involvement with immune responses, inflammation, cell proliferation and cell death, all of which are known to be regulated by NFKB. The overexpression of certain miRNAs is believed to lead to the repression of tumor suppressor genes that promote tumor survival and cell migration through NF-KB activation. miRNAs play a role in colonic carcinogenesis and their reduction by butyrate is an important mechanism of its anti-cancer effects.

Modifying the human genome, made possible by the CRIPSR technique, has its own wonderful upsides and equally daunting downsides. Permanent deletion of genes from the human genome is much more controversial than deletion of bacterial genes. Thus, one desirable aspect of the present invention is directed to the far less controversial modification of gut microbes resident in the human being to promote health and to trigger the desired immune responses as described herein.

CRISPR-Cas can be used on the various identified microbiome constituents to modify gene expression, including cutting of a gene, repress or activate a gene, etc. It can be employed to deliver desired regulators or any protein to a desired place on a genome of a microbe, thus permitting one to tailor the attributes of the microbiome of an individual to promote the health thereof, including the programmed triggering of particular immune responses in an infant. Because CRISPR-Cas acts before transcription occurs, it is able to be employed to target regulatory and other elements on the DNA of microbes that make up the microbiome. In certain embodiments, CRISPR-Cas is employed to deliver fluorescent markers to certain DNA sequences, thus permitting one to determine whether any particular sample has been treated in accordance with the present invention, thus ensuring, for example, identity of various materials, safety issues, types of enhanced soils, etc. This permits labeling of living cells with a desired color. Still other embodiments of the present invention are directed to the use of stool samples from Amish to transplant to other humans, especially expectant mothers, such that the attributes of the microbiome of the Amish can be enjoyed.

Certain embodiments rely upon the ability to deliver agents via mucosal adhesive strips, such as described, for example, in U.S. Pat. No. 8,701,671, which is fully incorporated herein by this reference. Thus, in various embodiments of the present invention, the engineering of communal bacteria with improved properties using a CRISPR/Cas system is employed to provide for the enhancement of health. In certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene, and most preferably the nucleotide sequence of interest comprises 16S ribosomal DNA (rDNA). In certain embodiments, the delivery vehicle is a bacteriophage. Thus, various embodiments of the present invention include the use of CRISPR-Cas, with the recognition that this system can be employed to benefit human health by modifying the bacterial and other microbe communities that humans have long been exposed to in a fashion such that the beneficial aspects of such microbes can be preserved, while the disadvantageous aspects can be "cut out" of the microbe d\DNA—rather than attempting to change or modify the DNA of a human.

The present invention is one way in which the human health concerns can be benefited directly by the use of a DNA deletion system without affecting the long term and permanent deletion of human genes. It is not believed to be obvious, let alone intuitive, that human health can be benefited by such a DNA deletion system used in a fashion that affects only gut microbes in a human's system. Moreover, the use of such a DNA modification system for microbes, but not for the direct deletion of genes from a human, and the use of such a system prior to the exposure of a human to such modified microbes, has not previously been done, especially with the added step of modifying select microbes.

In still other embodiments, employment of technology described in U.S. Pat. No. 9,131,884 to Holmes, incorporated herein by this reference, is employed to achieve desired further steps to address communication of biological disease status to a third party. For example, in certain embodiments, a medical device is associated with a mucosal strip that comprises a microarray having a bioactive agent capable of interacting with a disease marker biological analyte and a reservoir having at least one therapeutic agent, with the device able to release the therapeutic agent(s) from the medical device. In certain embodiments, at least two microchips with a microarray scanning device adapted to obtain physical parameter data of an interaction between the disease marker biological analyte and the bioactive agent is employed. A biometric recognition device is configured to compare the physical parameter data with an analyte interaction profile. The therapeutic agent releasing device controls the release of the therapeutic agent from the reservoir. The interface device facilitates communications between the microarray scanning device, biometric recognition device and the therapeutic agent releasing device. An energy source to power the medical device can take several forms, including biologically activated batteries that are preferably associated with the strip.

In certain other embodiments, sugar is used as a source of energy, notably glucose that is converted into different sugars via an enzymatic cascade to provide necessary energy to create an electrochemical gradient. This, in turn, is used to power an enzyme that synthesizes adenosine triphosphate (ATP). In contrast to natural catabolic pathways for cellular glucose oxidation, a preferred embodiment does not rely on ATP as an energy carrier. Instead, two redox enzymes oxidize glucose, generating reduced nicotinamide adenine dinucleotide (NADH) as the sugar is broken down. Another series of enzymes (as many as ten additional enzymes) further breakdown the sugars and feed them back to the redox enzymes to produce more NADH, with water and carbon dioxide being the only by-products. NADH is a reducing agent and acts as an electron shuttle that carries electrons in living cells from one molecule to another. NADH first transfers the electrons stripped from the glucose to a mediator with the help of an enzyme. The mediator then delivers these electrons to the battery's electrode, rendering it available to power an electronic device. Such a battery mimics the way a living cell transfers electrons from one molecule to another to generate power, it runs on renewable sugars, and has a high-energy storage density, rechargable providing an additional sugar solution. Malodextrin—a polymer made up of glucose subunits—may be employed together with particular different enzymes able to strip electrons from a single glucose molecule, thus harnessing the generated energy to power an electrical device. For such embodiments, and to comply with written description and enablement requirements, incorporated herein by the following references are the following patent publications: 2015/0216917 to Jones; 2015/0361436 to Hitchcock; 2015/0353901 to Liu; U.S. Pat. No. 9,131,884 to Holmes; 2015/0064138 to Lu; 2015/0093473 to Barrangou; 2012/0027786 to Gupta; 2015/0166641 to Goodman; 2015/0352023 to Berg.

Another aspect of the present invention includes the ability to load or impregnate mucosal strips with any number of active agents to achieve other desirable aspects, such as administration of particular vitamins, medicinal components, and certain modified bacteria, thus treating symptoms as well as causes of GERD. For example, providing strips that contain compounds thereon that affect the ability of *H. pylori* to thrive in an individual's stomach is one aspect of various embodiments of the present invention. Other aspects involve the purposeful administration of agents via an individual pressing with their tongue against an orally positioned mucosal strip that has encapsulated packets of such agent. Thus, a new administration device is provided such that various aspects of the present invention can be achieved by the use of such specialized strips.

In still other embodiments, the use of additional ingredients may provide for chemical binding, and, for example, the use of liposome technology can be employed. In some embodiments of the invention a part or all of the active ingredients on a mucosal adhesive strip are encapsulated within encapsulation structures selected to provide the desired degree of adhesion to the mucous membranes of the throat, and adapted to release the active ingredients slowly over time in situ. These encapsulation structures may be distributed within the base material in the strip composition. In one embodiment, the encapsulation structures comprise multilamellar microparticles. The multilamellar microparticles are selected to exhibit good adhesion to the mucous membranes of the throat, and are small enough to be effectively distributed in the strip. The multiple layers may be structured to give slow release of the active ingredient over the desired time period, so that a single strip dose gives sustained activity over time, for example providing for measurable activity for a sustained period of four or more hours, and ideally of for example 6 to 12 hours.

Preferably the strips of the present invention are made in a manner that do not dissolve in fewer than ten seconds, thus distinguishing the same from common breath strips widely available. The strips of the present invention may have a weight of from 30 to several hundred mg., preferably over 33 mg. Preferably, strips of the present invention have sufficiently high moisture content to impart the product with flexibility and to avoid becoming brittle, e.g. the strips should preferably avoid cracking when bent.

The strips of the present invention provide the requisite pliability and tensile strength necessary to securely adhere to a person's mucosal tissues for at least one hour, more preferably at least two hours, and even preferably a bioadhesive polymer is selected from the group consisting of polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts.

In certain embodiments, a mucosal adhesive strip has a coated surface for resisting bioadhesion that includes at least one patterned polymer including coating layer having a plurality of features attached to or projected into a base surface. The features each have at least one microscale ($<1$ mm) dimension and have at least one neighboring feature having a substantially different geometry. The patterned coating layer preferably provides an average roughness factor (R) of from 4 to 50. The coating layer resists or enhances bioadhesion as compared to the base surface. An article having a surface coating with topography for controlling bioadhesion comprises a base surface, at least one patterned polymer comprising coating layer including a plurality of spaced apart features attached to or projected into the base surface which provide at least a first feature spacing distance. The features each have at least one microscale dimension and at least one neighboring feature having a substantially different geometry. The coating layer provides an average roughness factor (R) of from 2 to 50, preferably being from 4 to 50. The coating layer resists or enhances bioadhesion as compared to the base surface.

Still other embodiments include the use of bacteria that have been modified to remove or disable one or more virulence factors of the particular bacteria. In this regard, one aspect of the present invention is directed to the modification of certain human-specific pathogens (including but not limited to *H. pylori*) by targeting one or more virulence factors thereof, preferably by using CRISPR-Cas or CRISPR-Cpf1 systems, to excise virulence factors genes, or at least portions thereof or transcriptional or translational controls therefore, such that such pathogenic pathogens are deprived of their undesired pathogenic characteristics. One of skill in the art can readily assess the number and identity of human-specific pathogens, as well as the particular virulence factors associated therewith, and can then, employing the CRISPR systems as referenced herein, remove, render incapable or otherwise disable the virulence facts of such microorganisms such that they no long pose a pathogenic threat to humans. In various aspects of the present invention, there is a purposeful exposure of individuals to such modified pathogens such that the population of the same, for example in the oral cavity or the human gut, competitively inhibits the infection of non-modified pathogenic microbes of the same species. Other embodiments provide for the delivery, via the strips as described herein of one or more of the following microorganisms selected from the group comprising *Lactobacillus lactis, Lactobacillus helveticus, Lactobacillus jensenii, Lactobacillus acidophilus, Lactobacillus* bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum, and Lactobacillus ingluviei.

Moreover, in preferred embodiments, the microbes modified are limited to those demonstrating human tropism such that undesired and unintended changes to other animals and organisms are not affected and that the only implications of such genomic alterations of human specific pathogens are restricted to such species in a manner that is not capable of affecting other than the particular human disease at issue. This can include, for example, modifications and/or employment of integrons, which are a two-component genetic recombination system present in the chromosome of many bacterial species. The integron incorporates mobile genes termed gene cassettes into a reserved genetic site via site-specific recombination, named the Integron/gene cassette system. The integron consists of three basic elements: an integrase gene, an attachment site and a promoter. These elements can be manipulated to, for example, decrease the ability of a particular bacteria in a person's gut from being able to effectively attach to epithelial tissue; or alternatively, to coaggregate with other bacteria.

To provide necessary and sufficient written disclosure and enablement of the various embodiments of the present invention, the following references are incorporated by reference in their entireties: U.S. Pat. No. 9,017,718 to Tan; 2014/0065218 to Lang et al.; U.S. Pat. Nos. 6,599,883; 8,383,201; 5,158,789; 2007/0218114 to Sorousch; 2004/0136923 to Davidson; U.S. Pat. No. 8,999,372 to Davidson; 2009/0196907 to Bunick; 2009/0196908 to Lee; 2003/0124178 to Haley; 2007/0293587 to Haley; 2010/0285098 to Haley; 2006/0204591 to Burrell; U.S. Pat. No. 7,087,249 to Burrelll; U.S. Pat. No. 6,210,699 to Acharya; U.S. Pat. No. 8,865,211 to Tzannis; 2014/0199266 to Park; U.S. Pat. No. 6,599,883 to Romeo; PCT/US2008/080362 to Dussia; 2007/0218114 to Duggan; 2004/0136923 to Davidson; 2011/142942 to Schobel; 2004/0120991 to Gardner et al.; Fuchs et al. U.S. Pat. No. 4,136,162; 2004/0136923 to Davidson; U.S. Pat. No. 4,163,777 to Mitra; U.S. Pat. No. 5,002,970 to Eby, III; 2004/0096569 to Barkalow et al.; 2006/0035008 to Virgallito et al.; 2003/0031737 to Rosenbloom; U.S. Pat. No. 6,919,373 to Lam et al.; 2005/0196358 to Georglades et al.; U.S. Pat. No. 3,832,460 to Kosti; 2002/002057 to Battey et al.; 2004/0228804 to Jones, et al.; U.S. Pat. No. 6,054,143 to Jones; U.S. Pat. No. 5,719,196 to Uhari; 2015/0150792 to Klingman; 2014/0333003 to Allen; 2014/0271867 to Myers; 2014/0356460 to Lutin; 2015/0038594 to Borges; U.S. Pat. No. 6,139,861 to Friedman; 2016/0206564 to Trachtman; 2016/0089405 to Lue; U.S. Pat. No. 7,901,925 to Bojrab and 2016/0333348 to Clube et al.; Zhang, et al., *Faecalibacterium Prausnitzii* Produces Butyrate to Maintain TH17/TREG Balance and to Ameliorate Colorectal Colitis by Inhibiting Histone Deacetylase 1, Gastroenterology, May 2018, Volume 154, Issue 6, Supplement 1, Page S-34; US Publication No. 20160206666 to Falb; Walker, et. al., Intracellular delivery of biologic therapeutics by bacterial secretion systems, Expert Reviews in Molecular Medicine, Vol. 19; e6; 1 of 15 (2017); Bosma, et al., Lactobacilli and pediococci as versatile cell factories—Evaluation of strain properties and genetic tools, Biotechnology Advances, (2017); 20160333348 to Clube, et al.; 20170067065 to Falb, et. al.; 20180258411 to, Kadiyala et. al., U.S. Pat. No. 10,022,457 to Peyman, et. al.; Zhang, et. al., *Faecalibacterium Prausnitzii* Produces Butyrate to Maintain TH17/TREG Balance and to Ameliorate Colorectal Colitis by Inhibiting Histone Deacetylase 1, Gatroenterology, May 2018, Volume 154, Issue 6, Supplement 1, Page S-34; US Publication No. 20160206666 to Falb; US 20150071957 to Kelly, et. al.; Walker, et. al., Intracellular delivery of biologic therapeutics by bacterial secretion systems, Expert Reviews in Molecular Medicine, Vol. 19; e6; 1 of 15 (2017); Bosma, et. al., Lactobacilli and pediococci as versatile cell factories—Evaluation of strain properties and genetic tools, Biotechnology Advances, (2017); Tian, et. al., *Faecalibacterium Prausnitzii* Prevents Tumorigenesis in a Model of Colitis-Associated Colorectal Cancer, Gastroenterology, (2017); US20180140698 to Clube, et. al. and US20180114592 to Apte.

Another aspect of the certain embodiments of the present invention is directed to a thin film mucosal layered strip that includes several layers, and in one particular embodiment, at least four layers, with a first layer comprising an odor impervious material, a second layer that comprises at least one encapsulated solvent, a third layer having a solvent absorbent material, and a fourth layer comprising an adhesive, wherein the solvent is encapsulated in a frangible enclosure and is present in an amount of at least about 0.5 ml.

Treatment agents can be encapsulated in such strips, such that antibiotics or co aggregation agents or LAB, etc. can be encapsulated in a manner that they can be released into the oral cavity at a time when the person so desires and/or when the strip dissolves to a certain extent, e.g. when the walls of the encapsulating shell is worn thin enough to fracture to release the agent(s). The manner in which a capsule can be fractured in order to release its solvent contents is variable and will be understood by those of skill in the art. Preferably, the capsule is constructed in a manner that it is sufficiently robust such that mere transport and packaging of the strips containing such capsules does not cause any leakage or breakage of such capsules. Instead, the design of capsules is such that they are frangible with a considerable amount of force being directly applied thereto once the strips are placed on a particular mucosal surface, such as on the soft palette of a human, such that the person's tongue, when pressing against such capsule, can cause it to fracture to release the contents of the capsule. In other embodiments, two or more different materials may be released.

The CRISPR-Cas system is preferably employed to excise the virulence factors of one or more of the following bacteria: *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum, Lactobacillus ingluviei* and preferably selected from the group comprising the following microorganisms deposited with the German Collection for Microorganisms and Cell Cultures where they are numbered as DSM 25972, DSM 25987, DSM 25988, DSM 25989, DSM 25973 and have been in accordance with the Budapest Treaty regarding International Recognition of the Deposition of Microorganisms for the purpose of patent deposition.

In a preferred embodiment of the invention, strips containing effective amounts of these bacteria are provided that are attached to the soft palate region of a person's mouth or on other mucosal surfaces. Other LAB that may be employed in various embodiments include the following: *Lactobacillus slaivarius* CICC 23174; *Lactobacillus plantarum* CGMCC 1.557, *Lactobacillus rhamnosus* ATCC 53103, and *Lactobacillus acidophilus* ATCC 4356.

The timeliness of being able to address an imminent cellular interaction by providing medications or beneficial agents directly to the tissue at issue by merely having one's tongue cause a frangible vesicle, encapsulation, etc. to release a desired agent to contact with the tissue, is a novel way in which to effectively stop a biological process before it progresses to a later stage, at which point the desired effect of the agent may not be efficacious.

Yet another embodiment of the present invention is directed to the modification of certain bacteria such that they achieve the desired production of acid in an individual's stomach, but without causing GERD. Thus, providing modified bacteria that produce gastrin, which triggers parietal cells in the stomach lining to produce more hydrochloric acid, is achieved so that invading microbes are killed. While *H. pylori* can be modified to achieve this feat, other bacteria can be modified to survive in the acid environment of the stomach, while also avoiding the detrimental aspects of native *H. pylori*. The objective is to populate the stomach microbiome with microbes that thrive in the gastric acid environment but without interfering with the stomach's natural defense mechanism. An abnormally low level of acidity in the stomach is a factor in various disease states.

It is believed that microorganisms residing in the GI tract can create chemicals that affect portions of the nervous system and muscle tissues in the GI tract that control the sphincter valve at the entrance of the stomach from the esophagus. Thus, certain embodiments of the present invention are directed to the purposeful administration to an individual's GI tract of modified bacteria, e.g. via CRISPR systems, to generate desired chemicals that control the sphincter valve in a manner to address GERD. Thus, in accordance with one or more embodiments, an effective amount of a medicament comprised of one or more suitable bacteria is administered to a person to prevent, mitigate or treat GERD, such bacteria comprising, e.g. one or more *Lactobacillus, Prevotella, H. pylori*, etc. Moreover, in certain embodiments, in addition to modified bacteria in an oral strip, such strip may also include desired amounts of drugs, such as PPI's. Thus, thin oral solvent cast films for the delivery of the proton pump inhibitor, omeprazole (OME) via the buccal mucosa can be provided.

One of skill in the art will appreciate that still other embodiments of the present invention are directed to aspects of human health that are similarly related to the proper balance and populations of bacteria in an individual's microbiome, and in particular, to the reduction in the likelihood of developing, preventing and treating of Parkinson's disease. Parkinson's disease is a neurodegenerative disorder characterized by a chronic and progressive loss of dopamine neurons in substantia nigra pars compacta, leading to movement disorders including dyskinesia, resting tremor, rigidity, and gait disturbance. Parkinson's disease is the second most common neurodegenerative disease worldwide and affects more than one percent of people older than sixty years of age and roughly four percent of those older than 85. Although causality of the disease is not known, chronic inflammation appears to play an important role in the pathogenesis of Parkinson's disease. Significant increase of inflammatory cytokines such as TNF-alpha, II-1beta and IFN-gamma in glial cells in the substantia nigra of Parkinson's patients has been observed. One aspect of the present invention is directed to reducing the likelihood of developing Parkinson's disease by modulation of an individual's microbiome. Reduction of certain bacteria in a person's microbiome correlates to a reduction in the likelihood that one will develop Parkinson's disease. Such bacteria include *Proteus* sp., *Bilophila* sp., and *Roseburia* sp. To avoid Parkinson's disease, increasing the populations of members of the microbiological families Lachnospiraceae, Rikenellaceae, and Peptostreptococcaceae, and *Butyricicoccus* sp. is a suggested way to prevent or treat the disease. Thus, in several embodiments, the present invention is directed to gene-microbiome interactions that address the etiology for Parkinson's disease by targeting the gut bacteria to promote enhanced motor control. Distinct microbes associated with Parkinson's disease, rather than general microbial stimulation, manifest disease symptoms. Increasing the populations in an individual suffering from Parkinson's disease from the bacteria family Lachnospiraceae and Ruminococceae and lowering the amount of gut microbiomes of Proteobacteria is one aspect of particular embodiments of the invention. With one goal being to achieve elevated relative concentration of butyrate in the gut. Thus, in general a treatment for Parkinson's disease involves the provision to an individual's microbiota bacteria that are found to be missing or in reduced numbers as compared to healthy individuals, and the reduction of pathogenic resident microbes in such patients. Parkinson's disease is but one of several diseases that involve the gut bacteria as a link to disorders, e.g. such as anxiety, depression, and autism, thus, various neurologic conditions are able to be treated by using the invention as set forth herein to address such conditions. For example, in various embodiments, oral administration of specific microbial metabolites to affect the ability of gut bacteria to regulate movement disorders is one objective of the present invention.

In still other particular embodiments, as discussed above with respect to the connections between the oral and gut microbiomes and the various diseases stemming from dysbiosis thereof, by controlling the inflammatory response associated with gingivitis, the subgingival nutrient supply to the subgingival microbiota will not be conducive to periodontal pathogen overgrowth. Thus, by addressing the inflammatory response of an individual, it is possible to control infection by modulating the subgingival microbiota of an individual so that it is predominated by commensal bacteria compatible with periodontal health. By maintaining periodontal health, the occasions for pathogenic bacteria to travel to other parts of the body, including the brain and blood vessels, one is able to prevent various diseases, including but not limited to Parkinson's disease, Alzheimer's Disease, heart disease, GERD, etc.

Other aspects of the present invention relate to the modulation of an individual's microbiome by the use of dietary supplements, for example, by the use of omega-3 polyunsaturated fatty acids, well recognized for their anti-inflammatory properties, in combination with the provision of beneficial bacteria as described herein. Still other embodiments are directed to the modulation of an individual's microbiome by the administration of particular antibiotics (often followed by the purposeful administration of bacteria to one's microbiome), such as a systemic antibiotic (tetracycline) and especially in combination with a nonsteroidal anti-inflammatory drug (e.g. ibuprofen). Such combinations are often administered in connection with the treatment of periodontal treatments, such as with non-surgical root surface debridement to reduce certain oral microbiome communities and to alter the same in a way to promote health. Other agents can be employed in various embodiments of the present invention, including the use of azithromycin, which possesses antibacterial and also exerts anti-inflammation properties, thus allowing a combination of antibiotic and anti-inflammatory capabilities with one agent.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method for reducing the likelihood of colorectal cancer in an individual human being, said method comprising: substantially reducing the human being's resident populations of gut microbes prior to administering a therapeutically effective amount of a bacterial formulation comprising *Faecalibacterium prausnitzii*; and providing fructan fiber inulin in an amount sufficient to reduce the pH in the colon of the human being to achieve acidifying of the colon to enhance intestinal $Mg^{2+}$ absorption by the human being.

2. The method of claim 1, wherein the *Faecalibacterium prausnitzii* bacteria employed are first isolated from a human being's stool.

3. The method of claim 1, wherein the *Faecalibacterium prausnitzii* bacteria employed are from the human being treated.

4. The method of claim 1, further comprising reducing *H. pylori* populations in the individual human being.

5. The method of claim 1, wherein the bacterial formulation comprises bacteria modified via a clustered regularly interspaced short pallindromic repeats (CRISPR) CRISPR associated protein (Cas) system to express p53.

6. The method of claim 1, wherein said bacterial formulation further includes a microbe selected from the group consisting of *Streptococcus, Veillonella, Fusobacterium* and *Treponema*.

7. The method of claim 1, wherein the bacterial formulation further comprises a bacterium selected from the group consisting of *Chlamydia, Shigella flexneri, Mycoplasma bacteria*, and *H. pylori*.

* * * * *